US00H002154H

(19) United States

(12) Statutory Invention Registration (10) Reg. No.: US H2154 H

Hradil et al. (43) Published: Apr. 4, 2006

(54) PROCESS FOR PREPARING R- AND S-ISOMERS OF (R)-5-(2-( (2-(2-ETHOXYPHENOXY)ETHYL)AMINO) PROPYL)-2-METHOXYBENZENESULFONAMIDE

(75) Inventors: Pavel Hradil, Bohunovice (CZ); Miroslav Urbasek, Olomouc (CZ); Lubomir Kvapil, Slatinice (CZ); Petr Slezar, Olomouc (CZ)

(73) Assignee: Farmak, a.s., Olomouc (CZ)

(21) Appl. No.: 10/680,966

(22) Filed: Oct. 8, 2003

(65) Prior Publication Data

US 2005/0079589 A1 Apr. 14, 2005

(51) Int. Cl.
*C07C 303/00* (2006.01)

(52) U.S. Cl. ..... 564/86

(58) Field of Classification Search ..... 564/86; 562/100

See application file for complete search history.

(56) References Cited

U.S. PATENT DOCUMENTS

2003/0109752 A1 * 6/2003 Hoorn et al. ..... 564/86

* cited by examiner

*Primary Examiner*—Aileen Felton

(74) *Attorney, Agent, or Firm*—Reising, Ethington, Barnes, Kisselle, P.C.

(57) ABSTRACT

A process for preparing optically pure enantiomers of R-(−) tamsulosin of formiula Ia and S-(+)tamsulosin of formula Ib by resolving racemic tamsulosin of formula I by means of (IR)-(−)-camphor-10-sulfonic acid and (1S)-(+)-camphor-10-sulfonic acid, resp., in an environment of organic solvents, water or mixtures thereof.

(Ia)

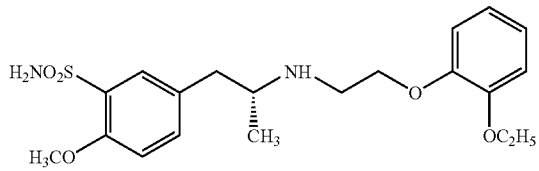

(Ib)

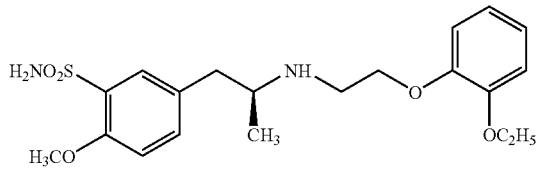

(I)

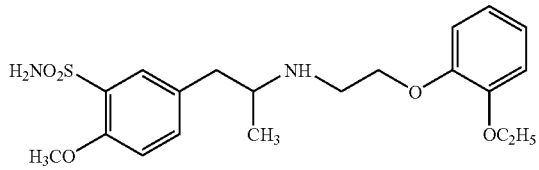

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR PREPARING R- AND S-ISOMERS OF (R)-5-(2-( (2-(2-ETHOXYPHENOXY)ETHYL)AMINO) PROPYL)-2-METHOXYBENZENESULFONAMIDE

TECHNICAL FIELD

The invention relates to a new process for preparing optically pure enantiomers of (R)-5-(2-((2-(2-ethoxyphenoxy)-ethyl)amino)propyl)-2-methoxybenzenesulfonamide [R-(−)-tamsulosin] of formula Ia and (S)-5-(2-((2-(2-ethoxyphenoxy)ethyl)amino)propyl)-2-methoxybenzenesulfonamide [S-(+)-tamsulosin] of formula Ib. R-(−)-tamsulosin show hypotensive activity and is used for the treatment of various diseases such as benign prostatic hypertrophy.

(Ia)

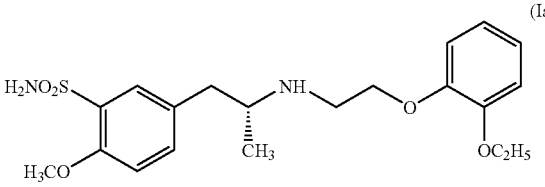

(Ib)

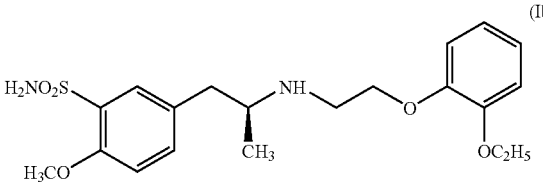

BACKGROUND ART

Up to date, no study has been described that would deal with preparation of the optically active R-(−)-tamsulosin (IB) and S-(+)-tamsulosin (Ib) by resolving the racemic tamsulosin of formula I.

(I)

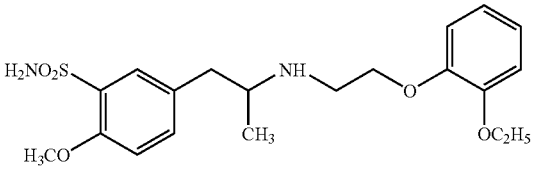

A first study, dealing with synthesis of racemic tamsulosin I only, is U.S. Pat. No. 4,703,063. Other consequential studies start from the optically active amine of formula II, followed by its conversion into the optically active R isomer Ia. This concept is used in, e.g., EP 380 144, or EP 257 787. Preparation of tamsulosin radioisotopes is described also in J. Labelled Comp. and Radiopharm Vol XXVII, No 2, 171. The authors prepare said substance by starting from a derivative of optically active 4-methoxyamfetamine and converting it, in consequential reactions, into the optically active amine II, (II)

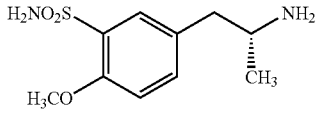

which, in turn, is converted, in a sequence of reactions, to desired R-(−)-tamsulosin Ia.

Drawbacks of the above processes include rather complicated manufacture of the optically active amine and the necessity of delicate choice of reaction conditions during many steps, in order to avoid racemization of optically pure intermediates. In case racemization, even a partial one, occurs, any method for processing the product is totally missing.

DISCLOSURE OF THE INVENTION

The above-mentioned drawbacks are overcome by the process of this invention, which is a process for preparing optically pure enantiomers of (R)-5-(2-((2-(2-ethoxyphenoxy)-ethyl)amino)propyl)-2-methoxybenzenesulfonamide [R-(−)-tamsulosin] of formula Ia and (S)-5-(2-((2-(2-ethoxyphenoxy)-ethyl)amino) propyl)-2-methoxybenzenesulfonamide [S-(+)-tamsulosin] of formula Ib.

(Ia)

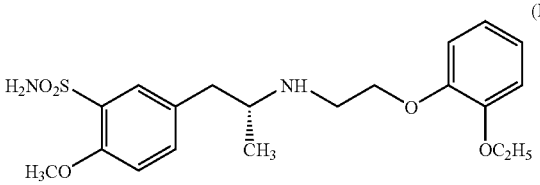

(Ib)

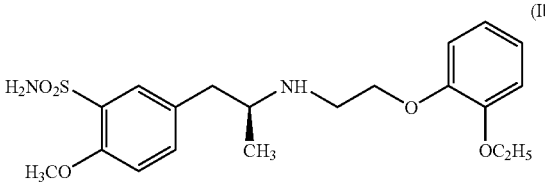

The substance of the inventions consists in carrying out:

(a) the resolution of racemic tamsulosin of formula I (I)

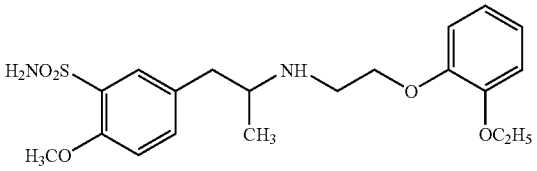

by the treatement with (1R)-(−)-camphor-10-sulfonic acid and (1S)-(+)-camphor-10-sulfonic acid, resp., in an environment of organic solvents, water or mixtures thereof;

(b) further purification of the crystallized salt of R-(−)-tamsulosin or S-(+)-tamsulosin by crystallizing form organic solvents, water or mixtures thereof, until the desired optical purity is obtained;

(c) from the salt of R-(−)-tamsulosin or S-(+)-tamsulosin is released, by treatment with alkalis, the base of formula Ia or the base of formula Ib, resp.

A further substance of the invention is that steps (a) and (b) are carried out in an environment of water.

A further substance of the invention is that steps (a) and (b) are carried out in an environment of alcohols.

Said process enables to obtain optical purity above 99%.

After R-(−)-tamsulosin Ia or S-(+)-tamsulosin Ib is isolated, it is converted into a pharmaceutically active salt by conventional means.

EXAMPLES

The process of the invention is further illuminated in the following examples. The examples are of an illustrative nature only and do not limit the scope of the invention in any way.

Example 1

To 200 ml methanol, 20 g racemic tamsulosin I are added. The resulting mixture is heated to ebullition. After the solids are dissolved, the solution is filtered with activated carbon. To the filtrtate, 11.5 g (1R)-(−)-camphor-10-sulfonic acid are added and the mixture is agitated until crystals precipitate. The precipitated crystal is sucked off and washed with methanol. Thereafter it is dissolved in boiling methanol, filtered with activated carbon. The precipitated product is filtered off. This operation is repeated three times. The obtained product is dissolved in methanol and alkalified with aqueous ammonia. The precipitated R-(−)-tamsulosin is sucked off, washed with water and dried at 60° C. The described process gives 1.9 g of (R)-(−)-tamsulosin of formula Ia, having an optical purity of 99.1% (as determined by capillary electrophoresis).

Example 2

To 400 ml methanol, 20 g racemic tamsulosin I are added. The resulting mixture is heated to ebullition, after dissolution of the solids the solution is filtered with activated carbon. To the filtrate, a solution of 11.5 g (1S)-(+)-camphor-10-sulfonic acid in methanol is added and the mixture is agitated until crystals precipitate. The precipitated crystal is sucked off, washed with methanol and dried. The described process gives a salt, containing 55% of (S)-(+)-tamsulosin Ib.

Example 3

2 g of a salt of (1S)-(+)-camphor-10-sulfonic acid with tamsulosin, containing 90% of (S)-(+)-tamsulosin Ib, are dissolved in 50 ml boiling water. Filtration with activated carbon, cooling down a crystallizing gives 1.3 g of a salt, containing 91.5% of (S)-(+)-tamsulosin.

INDUSTRIAL APPLICABILITY

The process for preparing optically pure enantimoers of (R)-5-(2-((2-(2-ethoxyphenoxy)-ethyl)amino)propyl)-2-methoxybenzenesulfonamide [R-(−)-tamsulosin] of formula Ia and (S)-5-(2-((2-(2-ethoxyphenoxy)-ethyl)amino)propyl)-2-methoxybenzenesulfonamide [S-(+)-tamsulosin] of formula Ib can be employed in favorable technical and economic conditions, obtaining at the same time a sufficiently high yield and high purity.

We claim:

1. A process for preparing optically pure enantiomers of (R)-5-(2-((2-(2-ethoxyphenoxy)-ethyl)amino)propyl)-2-methoxybenzenesulfonamide [R-(−)-tamsulosin] of formula Ia (Ia)

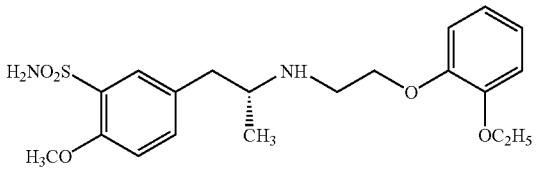

and (S)-5-(2-((2-(2-ethoxyphenoxy)-ethyl)amino)propyl)-2-methoxybenzenesulfonamide [S-(+)-tamsulosin] of formula Ib (Ib)

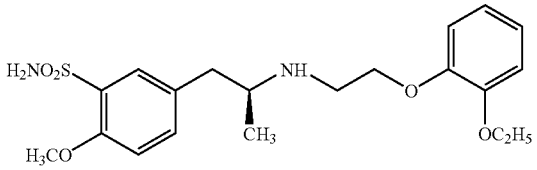

comprising:

(a) the resolution of racemic tamsulosin of formula I (I)

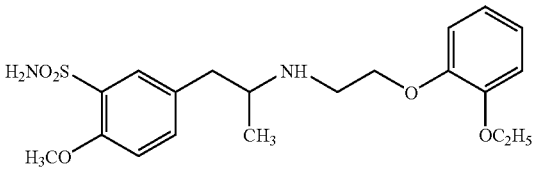

by the treatment with (1R)-(−)-camphor-10-sulfonic acid and (1S)-(+)-camphor-10-sulfonic acid, resp., in an environment of organic solvents, water or mixtures thereof;

(b) further purification of the crystallized salt of R-(−)-tamsulosin or S-(+)-tamsulosin by crystallizing form organic solvents, water or mixtures thereof, until the desired optical purity is obtained;

(c) from the salt of R-(−)-tamsulosin or S-(+)-tamsulosin is released, by treatment with alkalis, the base of formula Ia or the base of formula Ib, resp.

2. The process of claim 1 wherein steps (a) and (b) are carried out in an environment of alcohols.

3. The process of claim 1 wherein steps (a) and (b) are carried out in an environment of water.

4. A process which comprises:

(a) preferentially precipitating one diastereomeric camphor sulfonate salt of tamsulosin from a solution containing a pair of diastereomeric camphor sulfonate salts of tamsulosin to form diastereomeric enriched precipitate and diastereomeric enriched solute.

5. The process according to claim 4, which further comprises forming said solution by dissolving a solid mixture of a pair of diastereomeric camphor sulfonate salts of tamsulosin in a solvent.

* * * * *